(12) United States Patent
Schneider et al.

(10) Patent No.: US 12,740,798 B2
(45) Date of Patent: Sep. 22, 2026

(54) SURGICAL INSTRUMENT AND STEERING MECHANISM THEREFOR

(71) Applicant: KARL STORZ SE & CO. KG, Tuttlingen (DE)

(72) Inventors: Janosz Schneider, Donaueschingen (DE); Dominik Längle, Mülheim (DE); Jochen Stefan, Wald (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 307 days.

(21) Appl. No.: 18/291,640

(22) PCT Filed: Jul. 25, 2022

(86) PCT No.: PCT/EP2022/070791

§ 371 (c)(1),
(2) Date: Jan. 24, 2024

(87) PCT Pub. No.: WO2023/006664

PCT Pub. Date: Feb. 2, 2023

(65) Prior Publication Data

US 2025/0009376 A1 Jan. 9, 2025

(30) Foreign Application Priority Data

Jul. 28, 2021 (DE) ......................... 102021119527.6

(51) Int. Cl.
*A61B 17/29* (2006.01)
*A61B 17/00* (2006.01)

(52) U.S. Cl.
CPC .... *A61B 17/29* (2013.01); *A61B 2017/00398* (2013.01); *A61B 2017/00477* (2013.01);
(Continued)

(58) Field of Classification Search
CPC ............ A61B 17/2804; A61B 17/2812; A61B 17/2816; A61B 2017/00323;
(Continued)

(56) References Cited

U.S. PATENT DOCUMENTS 5,454,827 A 10/1995 Aust et al.
7,699,855 B2 4/2010 Anderson et al.
(Continued)

FOREIGN PATENT DOCUMENTS

DE 102019121092 A1 2/2021
WO 2014004242 A1 1/2014
WO 2020218920 A2 10/2020

OTHER PUBLICATIONS

International Search Report, Application No. PCT/EP2022/070791, mailed Nov. 17, 2022. ISA/European Patent Office.
(Continued)

*Primary Examiner* — Martin T Ton
(74) *Attorney, Agent, or Firm* — Brooks Kushman P.C.

(57) ABSTRACT

A steering mechanism for a surgical instrument having a shaft. The steering mechanism is disposed on the shaft and the shaft includes a bending mechanism. The steering mechanism has two motor-driven drives configured to spatially align a swash plate which controls the distal bending mechanism. The first drive has a first drive shaft driven by a first motor and is operatively connected to a first traction pulley of a first drive wheel via a first traction mechanism. The second drive has a second drive shaft driven by a second motor and is operatively connected to a second traction pulley of a second drive wheel via a second traction mechanism. The first and second drive wheels each a bevel wheel rim, wherein the swash plate is located between the two drive wheels, and the bevel wheel rims being positioned facing each other on the axis of rotation.

18 Claims, 5 Drawing Sheets

(52) U.S. Cl.
CPC ................. *A61B 2017/2927* (2013.01); *A61B 2017/2932* (2013.01)

(58) Field of Classification Search
CPC .. A61B 2017/00327; A61B 2017/2912; A61B 2017/1932; A61B 2017/2947; A61B 2017/2933; A61B 2017/2938; A61B 2017/2939; A61B 2017/2941; A61B 2017/294
See application file for complete search history.

(56) References Cited

U.S. PATENT DOCUMENTS

| | | | | |
|---|---|---|---|---|
| 10,105,128 | B2 | 10/2018 | Cooper et al. | |
| 11,191,425 | B2 * | 12/2021 | Xu | A61B 1/0055 |
| 2005/0090809 | A1 | 4/2005 | Cooper et al. | |
| 2008/0287963 | A1 * | 11/2008 | Rogers | A61B 1/008 606/130 |
| 2019/0231331 | A1 * | 8/2019 | Xu | A61B 17/29 |
| 2022/0061634 | A1 * | 3/2022 | Thissen | A61B 34/71 |

OTHER PUBLICATIONS

International Preliminary Report on Patentability, Application No. PCT/EP2022/070791, mailed Jan. 18, 2024. ISA/European Patent Office.

* cited by examiner

D
13
15'
31
18'
21
A
19'
17a'
16a'
15
16b'
18
16d'
16'
19
12
33
16c
16
2
17a
25
3
B
17'
17
C'
C

SURGICAL INSTRUMENT AND STEERING MECHANISM THEREFOR

CROSS-REFERENCE TO RELATED APPLICATIONS

This application is the U.S. national stage of PCT/EP2022/070791 filed on Jul. 25, 2022, which claims priority of German Patent Application No. 10 2021 119 527.6 filed on Jul. 28, 2021, the contents of which are incorporated herein.

TECHNICAL FIELD

The disclosure relates to a surgical instrument and a steering gear for same.

BACKGROUND

The prior art has disclosed surgical instruments which can be guided by hand or by a robot and which comprise tools, the tool tip of which can be pivoted by means of a plurality of meshing pivot members. These pivot members are connected by way of a multiplicity of steering wires or steering cables in order to attain delicate tool control. A more uniform force distribution in all deflection directions can be obtained by way of a large number of thin steering wires in comparison with a few thicker steering wires For example, a generic surgical instrument is known from U.S. Pat. No. 5,454,827, in which the distal-side pivot members are coupled via four steering wires to a spatially adjustable wobble plate arranged on the proximal side, in such a way that a movement of the spatially adjustable wobble plate causes a corresponding relative movement of the distal-side pivot members and hence a pivoting of the tool tip, with the movement of the spatially adjustable wobble plate being implemented manually by way of a type of joystick that is directly coupled therewith.

The design of the drive for the steering wires with the spatially adjustable wobble plate, on which all steering wires are mounted, is advantageous in that this enables a spatially compact structure and only requires the movement of one component to address all steering wires.

U.S. Pat. No. 7,699,855 has disclosed a surgical instrument having an interface that enables the connection of the instrument to a robotic arm. In this case, all drives controlling the instrument are arranged in the robotic arm. The transfer of the rotary angles from drives to the instrument is implemented by way of coupling plates in a common separation plane.

WO 2014/004242 likewise describes such an interface, wherein the drives are installed in the robotic arm.

The aforementioned design is linked to a complex structure and an indirect control afflicted by play. The drives are not arranged directly in the surgical instrument, resulting in a nonlinear transmission behavior during the control of the wobble plate, which can only be modeled poorly in software.

U.S. Pat. No. 10,105,128 B2 also discloses a control of such a tool tip; in that case, this is implemented by way of a mechanism comprising toothed lock washer segments and joint rods for transmitting the movement of the drives to the wobble plate.

SUMMARY

Proceeding from this prior art, it is an object of the present disclosure to provide an improved steering gear for a surgical instrument which has a drive of the spatially adjustable wobble plate with a linear transmission behavior and a space-saving structure at the same time.

This object is achieved by a steering gear having the features of claim 1.

The further object of providing a surgical instrument whose spatially adjustable wobble plate is driven by a structurally simple and space-saving steering gear is achieved by the surgical instrument having the features of independent claim 9.

Developments and preferred embodiments of the steering gear and the surgical instrument are defined in the dependent claims.

According to a first embodiment of the steering gear according to the disclosure for a surgical instrument, the steering gear is arranged at the proximal end of a shaft. The shaft defines a longitudinal axis B and comprises a deflection mechanism at the distal end. Further, the steering gear comprises two motorized drives. It is designed to spatially align a wobble disk plate by way of the adjustment angles of the two drives, the wobble plate being designed to control the distal deflection mechanism of the surgical instrument.

According to the disclosure, the first drive comprises a first drive shaft which is driven by a first motor and operatively connected to a first traction mechanism plate of a first drive wheel via a first traction mechanism. The first traction mechanism is arranged between the first traction mechanism plate and a spindle which is seated on the first drive shaft. The first drive shaft defines a first drive axis C.

The second drive comprises a second drive shaft which is driven by a second motor and operatively connected to a second traction mechanism plate of a second drive wheel via a second traction mechanism. The second traction mechanism is arranged between the second traction mechanism plate and a spindle which is seated on the second drive shaft. The second drive shaft defines a second drive axis C'.

In this case, the first and the second drive wheel are designed as double gear wheels and each comprise the corresponding traction mechanism plate and a bevel gear rim present on the respective backward side. The wobble plate is arranged between the two drive wheels, which have a common axis of rotation A, wherein the bevel gear rims are arranged facing one another on the axis of rotation A.

As a result of the arrangement according to the disclosure of the motors offset by 90° from the common axis of the double gear wheels, horizontal installation space in view of the alignment of the wobble plate is saved in the direction of the common axis A of the double gear wheels.

Advantageously, the drive wheels are equipped with a dual functionality; thus, they serve not only to actuate the wobble plate but also, at the same time, as movement transmission media for the rotational movement of the motors to further components of the steering gear and, ultimately, of the wobble plate. This achieves a direct deflection of the drive axes without requiring an additional gear stage or play, whereby a compact structure is obtained.

Preferably, the traction mechanism plate and bevel gear rim are arranged back to back, wherein the double gear wheels particularly preferably have a one-piece embodiment, whereby a compact and space-saving structure can be obtained.

A further embodiment of the steering gear according to the disclosure provides for the first traction mechanism and the second traction mechanism to be closed or not closed belts or cables. Thus, use can be made of traction mechanisms with different cross sections, for example cables with a round cross section or belts with a flat, rectangular cross section. Multi-member chains may also be suitable traction mechanisms. The materials used are matched to the force to be applied in the traction mechanism drive; in addition to traction mechanisms made of high tensile strength metals or metal alloys, for example steel wires, use can also be made of plastics or composites, for example carbon or other fiber-reinforced plastics. The shape of the traction mechanisms can be a closed shape, with the result that a ring is present all around. Traction mechanisms that are not closed can also be used, wherein the free ends can be fastened both to the spindle and to the traction mechanism plate. The traction mechanism drives offer a reliable option for effectively driving the wobble plate.

In a preferred embodiment of the steering gear according to the disclosure, the two drive axes C, C' may run parallel to one another, wherein the drive axes run perpendicular to the common axis A. A so-called axially parallel arrangement of the motors enables a compact and hence space-saving arrangement of the components of the steering gear. Further, the parallel arrangement of the motors achieves an arrangement close to the main axis of the surgical instrument and hence improves the force transmission. An alternative embodiment of the steering gear according to the disclosure provides for each of the motors, by way of its respective spindle, to be able to be in any radial position pointing away from the respective drive wheel rim. An arbitrary arrangement of the drives around the common axis of rotation of the double gear wheels in conjunction with a suitable operative connection of spindle and traction mechanism plate allows a multiplicity of different arrangements.

In yet a further embodiment of the steering gear according to the disclosure, the spindle has a groove all round, in which the traction mechanism is guided. In this case, the traction mechanism lies in the groove with a certain amount of pretension, which arises due to the appropriately chosen traction mechanism and the arrangement of spindle and traction mechanism plate. Advantageously, the movement of the traction mechanism is guided in this way, with the result that the traction mechanism cannot slip off the spindle.

Further, a preferred embodiment of the steering gear according to the disclosure provides for the spindle to comprise a spindle nut. The spindle nut is a safety component which, like the groove, also prevents the traction mechanism from slipping out of the groove and further falling from the spindle, especially in the case of fast directional changes in the movement of said traction mechanism.

In a further embodiment of the steering gear according to the disclosure, the traction mechanism plate comprises a groove all around, with which the traction mechanism is in contact. As already held true for the spindle, this groove serves for secured and directed guidance of the traction mechanism, now at the traction mechanism plate. This also allows the traction mechanism to be tensioned as a result of the arrangement of the spindle at a predetermined distance, with the result that a certain frictional force can be exerted on the traction mechanism. As a result, the traction mechanism can be moved in more targeted fashion.

In yet a further or else alternative embodiment of the steering gear according to the disclosure, the traction mechanism plate has a groove all round, in which the ends of the not closed traction mechanism are fastened using sliding blocks. This embodiment allows the use of not closed traction mechanisms, the free ends of which are fastened captively in the groove of the traction mechanism plate by means of the sliding blocks.

In a further embodiment of the steering gear according to the disclosure, the wobble plate may be coupled to a third gear wheel. The third gear wheel as part of the wobble plate gear meshes with the two bevel gear rims of the two double gear wheels. The axis of rotation D of the third gear wheel is at right angles to the common axis A of the driven double gear wheels. Advantageously, the three meshing gear wheels transmit any movement of the two driven gear wheels directly to the third gear wheel coupled to the spatially adjustable wobble plate, with the result that the adjusting movements of the drives are transmitted thereby to the wobble plate, which can be tilted or pivoted about the common axis A and the axis of rotation D as a result.

Additionally, in a further embodiment of the steering gear according to the disclosure, the wobble plate can be coupled to a fourth gear wheel which is coupled to the two bevel gear rims of the two double gear wheels and arranged on the side of the wobble plate facing away from the third gear wheel. As a result, the all-round gear chain is closed and a uniformly all-round force distribution without play is ensured.

The disclosure also relates to a surgical instrument comprising a shaft, an actuation unit arranged at the proximal end of the shaft, and a tool arranged at the distal end of the shaft. The tool comprises a tool tip which can be deflected by means of a distal deflection mechanism. The deflection mechanism can be controlled or aligned by means of a wobble plate that is spatially alignable by means of two drives, for the purposes of which the surgical instrument comprises a steering gear according to the disclosure, wherein the two drives are part of the steering gear according to the disclosure, which is designed to transfer the adjustment angles of the two drives to the spatial alignment of the wobble plate in order thus to control the deflection mechanism.

As a result of the steering gear according to the disclosure, the surgical instrument can be constructed in structurally simple and space-saving fashion, with the result that a simple connection to a robotic arm can be enabled, in the case of which the movement of the drives can be transmitted linearly to the tool tip. The consequence is a precisely controllable use of the surgical instrument.

To three dimensionally adjust the spatially adjustable wobble plate despite the coupling for conjoint rotation with the third gear wheel which meshes with the two bevel gear rims of both two double gear wheels, which is to say to be able to overlay the tilt or pivot movements with a rotation of the wobble plate about the longitudinal axis, a preferred embodiment of the surgical instrument can provide for the wobble plate, via a bearing ring, to be mounted so as to be rotatable about the longitudinal axis B of the shaft in a steering ring that is coupled for conjoint rotation with the third gear wheel. For the rotative coupling of the wobble plate with a main shaft running coaxially to a longitudinal axis B of the shaft, the wobble plate can be gimbal-coupled with the main shaft. Hence, the tool tip can be rotated about the longitudinal axis of the shaft by means of the wobble plate, in addition to the pivoting or tilting relative to the longitudinal axis of the shaft by way of the two drives and by way of the main shaft.

To form the gimbal mount of the spatially adjustable wobble plate, an embodiment of the surgical instrument according to the disclosure may provide for the wobble plate to be pivotably mounted on a universal joint plate by way of two bearing pins arranged offset from one another by 180°, wherein the universal joint plate is pivotably mounted on the main shaft by way of two bearing pins arranged offset from one another by 180°, and wherein the bearing pins of the wobble plate and the universal joint plate are arranged offset from one another by 90°. The gimbal suspension enables a movement guidance in all three spatial axes, whereby the tool tip can be controlled in targeted fashion. As an alternative to a universal joint plate with two pin pairs crossed at right angles for the gimbal mount of the wobble plate on the main shaft, an advantageous embodiment may, for gimbal mounting purposes, provide for the main shaft to comprise two guide grooves present in its outer face, said guide grooves extending diametrically and along the main shaft, wherein the wobble plate, which has an annular embodiment with an outer side and an inner side, comprises two diametrically and radially inwardly pointing pins arranged on the wobble plate. Each one of the two pins securely assembled on or in the wobble plate engages in one of the guide grooves introduced in the main shaft on both sides, with the result that a rotary angle of the shaft is transferable to the wobble plate. Advantageously, this yields a rotationally rigid connection between the main shaft and wobble plate, which allows a rotary angle transfer even in the case of a large angle offset (±40° and more) and axial offset, and which in the process has a very compact design, and is simple to produce and assemble. However, for a gimbal mount of a wobble plate on a main shaft, use could in principle also be made of a curved tooth coupling despite a relatively small angular offset, a constant velocity joint despite the complicated fabrication and complex assembly, or an integrally bonded coupling, which is frequently linked to a play-affected rotary angle transfer.

In a further embodiment of the surgical instrument according to the disclosure, steering wires connected to the wobble plate of the steering gear run in the longitudinal direction of the shaft. Preferably, the steering wires may be detachably fastened to the wobble plate, for example by means of a clamping connection, so that, in the case of damage, the steering wires can easily be replaced. The wobble plate being rotationally coupled to the main shaft and being rotatably mounted in the steering ring as a result of the bearing ring, said steering ring being coupled for conjoint rotation with the third gear wheel, further advantageously prevents twisting of the steering wires when pivoting the tool tip relative to the longitudinal axis and when performing a rotation about the longitudinal axis of the shaft.

Compared to known structures, this structure is advantageous not only in that it is possible to use a small number of steering wires, specifically only four steering wires, and a purely manual actuatability of the spatially adjustable plate serving as drive for the steering wires, but also in that a multiplicity of steering wires can be chosen freely, thereby enabling a delicate and reproducible adjustment of the distal-side pivot members.

Also, an even further embodiment of the surgical instrument according to the disclosure provides for the fourth gear wheel to be coupled to the wobble plate via a bearing ring with the steering ring, wherein the fourth gear wheel is freely rotatable vis-à-vis the third gear wheel. This fourth gear wheel closes the all-round gear chain and thus ensures an all-around and play-free force distribution.

In a further embodiment of the surgical instrument according to the disclosure, an actuation element is axially displaceably mounted in the shaft and is operatively connected to the actuation unit on the proximal side. The distal deflection mechanism of the tool tip able to be deflected consists of pivot members which are arranged at the distal end of the shaft and connected to the wobble plate of the steering gear by way of steering wires running in the longitudinal direction of the shaft. Preferably, the steering wires can be releasably clamp-mounted on the wobble plate by means of a clamping connection so that, in the case of damage, the steering wires can easily be replaced. Alternatively, the steering wires may also be fastened to the wobble plate by means of welding or cramping, for example.

In a further embodiment of the surgical instrument according to the disclosure, a radial distance of the steering wires from the longitudinal axis of the shaft is greater at the wobble plate than at the proximal end of the shaft, from where the steering wires emerge. In this case, the steering wires may extend directly from the proximal end of the shaft to the wobble plate, wherein the steering wires form an angle of less than 90° in relation to a plate surface of the wobble plate. Alternatively, a fan plate can be arranged on the main shaft distally in front of the wobble plate, said fan plate increasing the radial distance of the steering wires, which emerge from the proximal shaft end, from the longitudinal axis of the shaft such that the steering wires run approximately parallel to one another between the fan plate and the wobble plate and, in relation to a plate surface of the wobble plate, form an angle of approx. 90°. The variant without fan plate may be preferred on account of the smaller installation space requirements. As a result of increasing the radial distance of the steering wires from the longitudinal axis of the shaft, for example from a diameter of 4 mm to a diameter of 18 mm, it is not only the assembly and fabrication of the drive of the steering wires which is equipped with the spatially adjustable plate that is simplified, but also the adjustment angles of the spatially adjustable plate or, as a consequence of the increased lever, the forces required for deflection that is/are reduced, which is done in order to obtain a pivot angle of the tool tip that corresponds to the extent of the diameter increase.

Cutouts for the steering wires and the actuation element may be formed in the gear rims of the third gear wheel and fourth gear wheel in order to avoid a collision of the gear wheels with the steering wires and optionally with the actuation element when the third and fourth gear wheel are pivoted relative to the longitudinal axis of the shaft.

The surgical instrument according to the disclosure is advantageous in that many thin steering wires can be used to control the pivotable tool tip and that, on account of the motorized drive for the spatially adjustable plate on which the steering wires are mounted proximally, this control is sensitive, precise and reproducible.

Further embodiments of the steering gear and surgical instrument, and some of the advantages connected to these and further embodiments, are rendered clear and better understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description, and the claims contain numerous features in combination. A person skilled in the art will advantageously also consider the features on an individual basis and combine them to form further advantageous combinations.

DETAILED DESCRIPTION OF PREFERRED EMBODIMENTS

Figure 1:
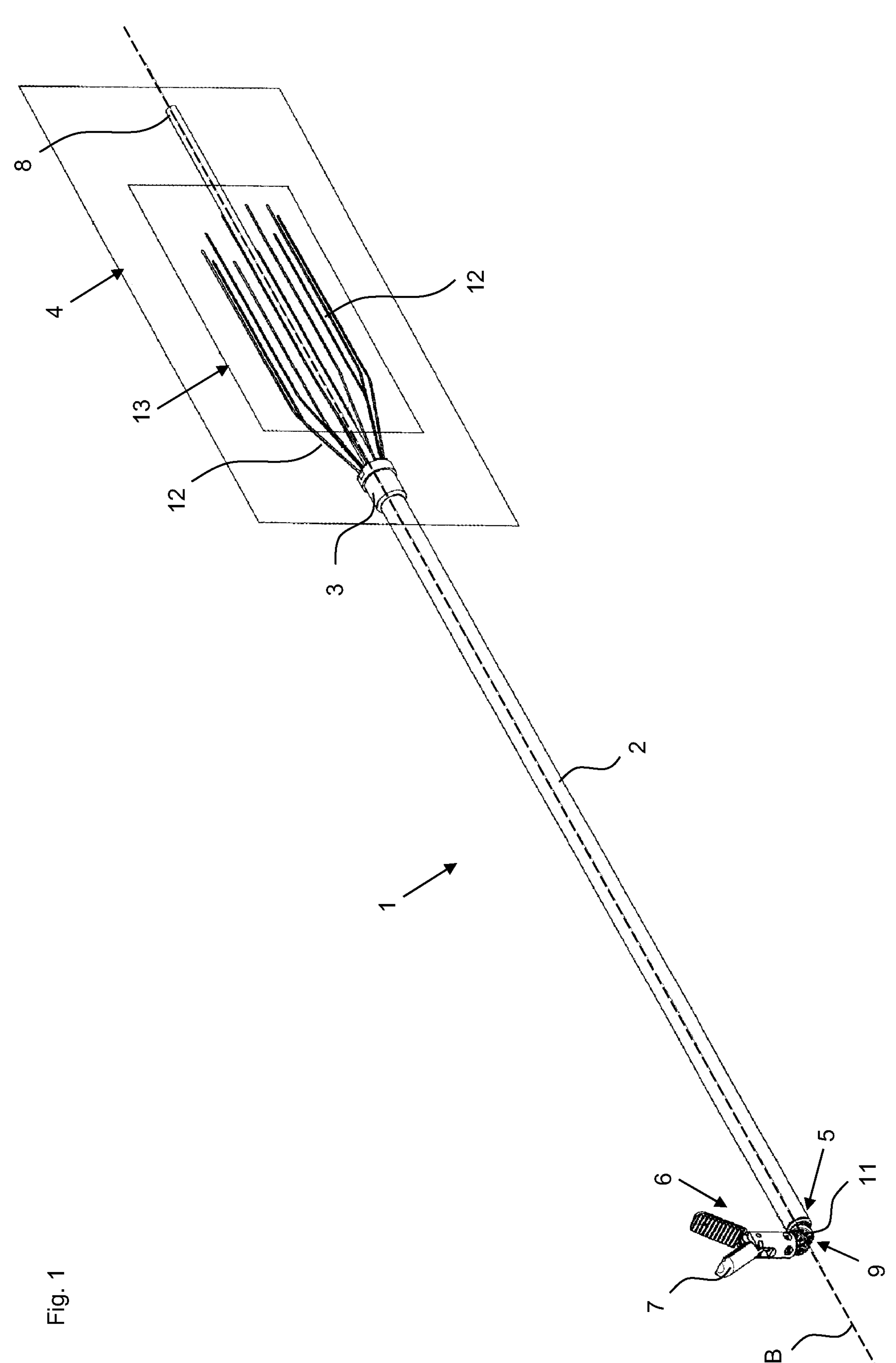
FIG. 1 shows a perspective view of the surgical instrument with a schematically depicted actuation unit.

FIG. 1 shows a surgical instrument 1 with a hollow shaft 2 which comprises a schematically depicted actuation unit 4 arranged at the proximal end 3 of the shaft 2 and a tool tip 6 arranged at the distal end 5 of the shaft 2. The tool tip 6 is connected to an instrument 7, wherein the instrument 7 can be actuated by way of an actuation element 8 which is axially displaceably mounted in the shaft 2 and, on the proximal side, operatively connected to the actuation unit 4. The actuation unit 4 can be a manually actuatable handle, or else a component designed for robotic use, which is to say a component that is actuatable without manual assistance as well.

For example, the instrument 7 of the tool tip 6 can be a tool provided with jaws, as depicted in FIG. 1, or else an endoscope, an applicator, or the like.

The tool tip 6 is pivotable relative to the longitudinal axis B of the shaft 2 by way of a joint mechanism 9, wherein the joint mechanism 9 consists of pivot members 11 which are arranged at the distal end of the shaft 5 and connected via steering wires 12 running in the longitudinal direction of the shaft 2 to a drive 13 arranged at the proximal end 3 of the shaft 2, in such a way that a movement of the proximal-side drive 13 causes a corresponding relative movement of the distal-side pivot members 11 and hence a pivoting of the tool tip 6.

Even though exclusive use is made of the term steering wires hereinabove and below, from a functional point of view use can also be made of steering cables, which is why the term steering wires should also be understood synonymously as steering cables in this text.

The actuation element 8, which is axially displaceably mounted in the shaft 2 and serves to actuate the instrument 7 for example consisting of two jaw parts, is in the form of a push/pull rod in the embodiments depicted.

In the surgical instrument 1 depicted in the drawings and described below, the drive 13 for the steering wires 12 is in the form of a motorized drive 13.

The core of the drive 13 is a spatially adjustable wobble plate 14 (FIGS. 2, 4, and 6), on which the steering wires 12 are mounted such that a displacement of the wobble plate 14 causes a pivoting of the tool tip 6 by way of the steering wires 12 mounted on said wobble plate. The wobble plate 14 can be displaced using the motorized drive 13; with it, it is possible to control the steering wires 12 for pivoting the distal-side pivot members 11 or tool tip 6 precisely, delicately in very small increments, and also in reproducible fashion. Moreover, the number of steering wires 12 to be used for a motorized steering gear 13 can be chosen quite freely.

Figure 2:
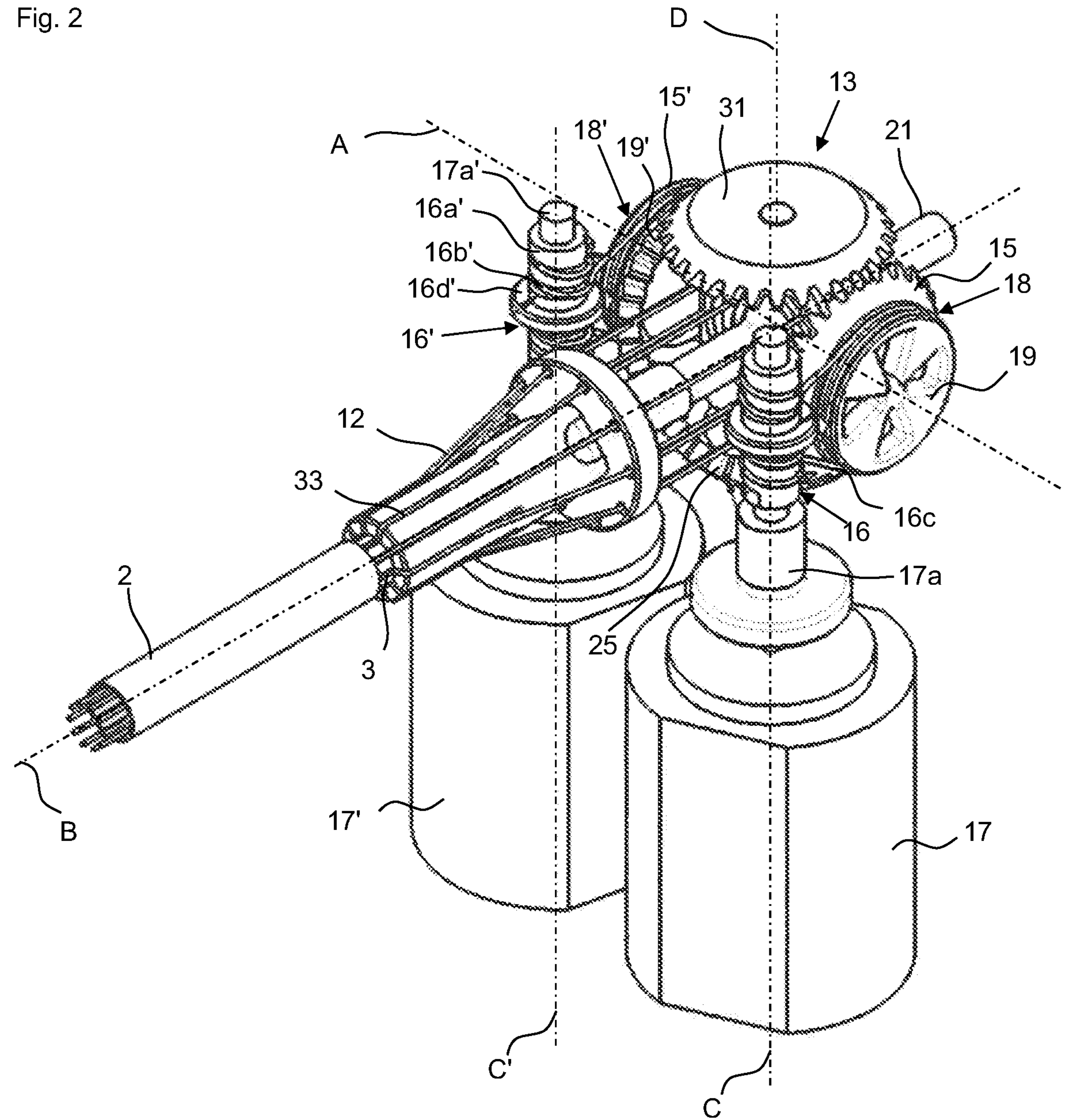
FIG. 2 shows a perspective detailed view of a first embodiment of the steering gear according to the disclosure.
Figure 4:
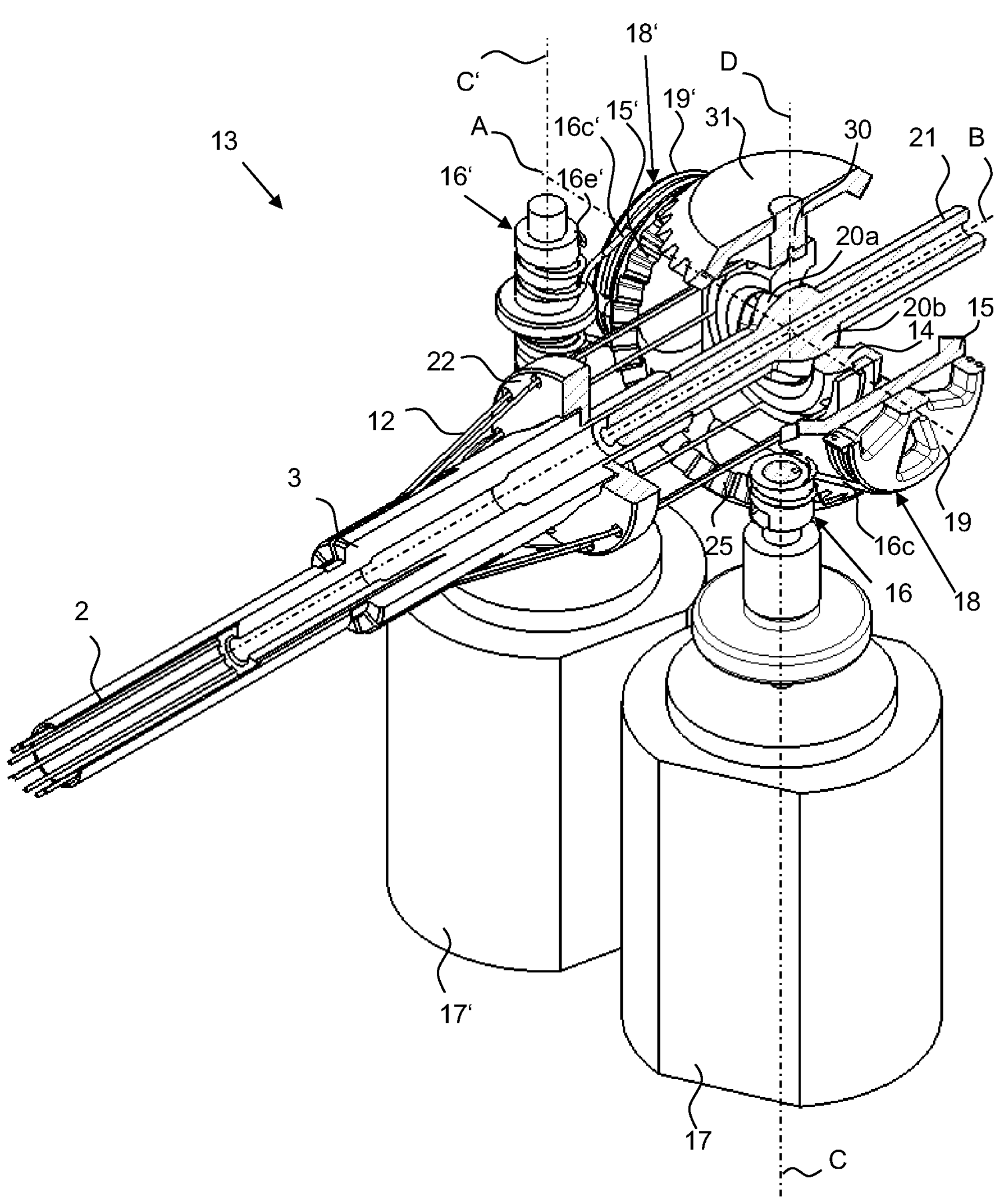
FIG. 4 shows a partly cut perspective view corresponding to FIG. 2.
Figure 5:
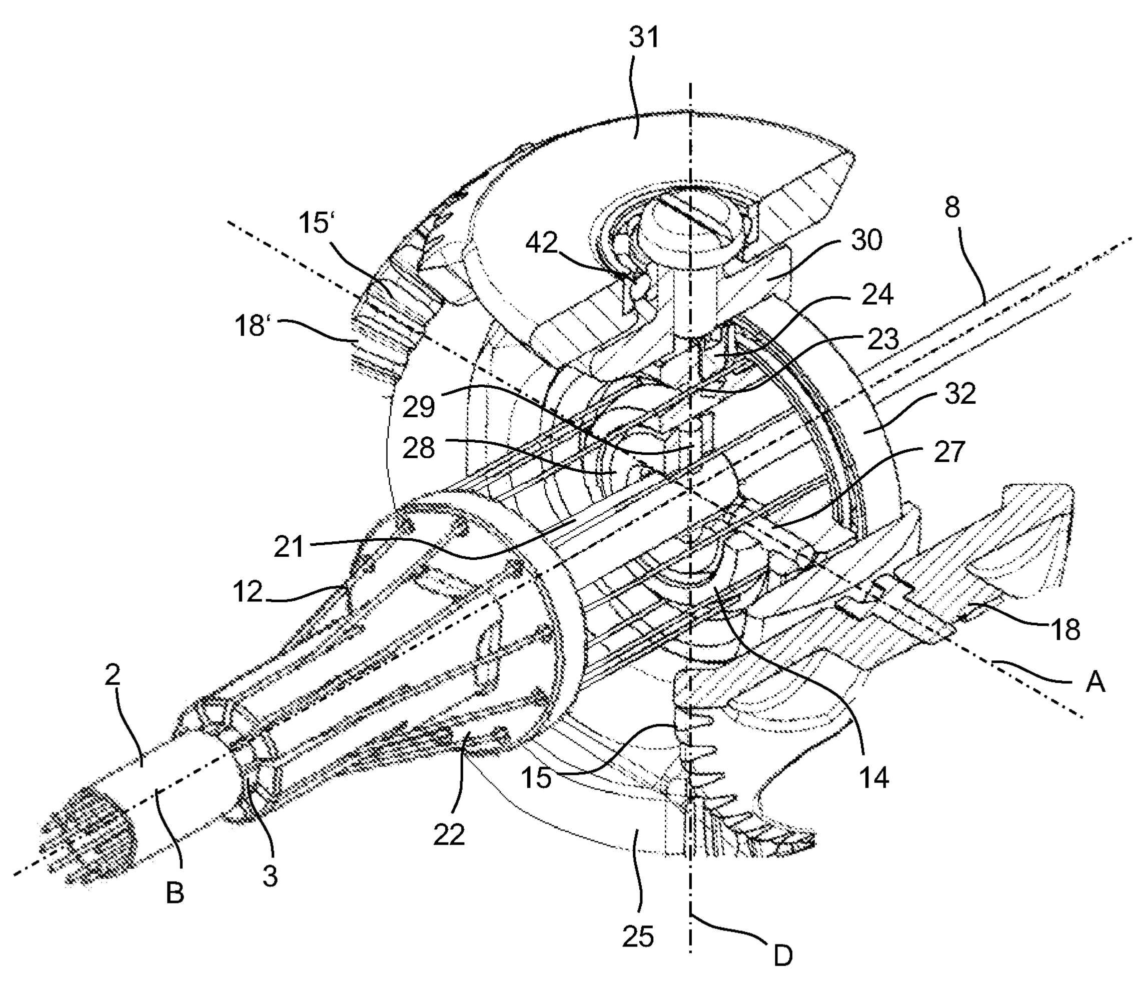
FIG. 5 shows a perspective, partly cut detailed view of an alternative wobble plate mount.

FIGS. 2 and 4 and FIG. 5 depict the steering gear 13 in simplified fashion, wherein the steering gear 13 comprises a wobble plate 14 at the center. Four gear wheels are connected to the wobble plate 14. A third gear wheel 25 and a fourth gear wheel 31 are arranged above and below the wobble plate 14 and operatively coupled to the wobble plate 14. That is to say, a movement of one of these gear wheels 25, 31 has a direct movement of the wobble plate 14 as a consequence. Double gear wheels 18, 18' respectively arranged to a left and right side mesh with the gear wheels 25, 31. To this end, the double gear wheels comprise bevel gear rims 15, 15', which mesh directly in the gear rims of the gear wheels 25, 31. On sides facing away from one another and along their center axis A, which also forms the common axis of rotation of both double gear wheels 18, 18', the double gear wheels 18, 18' comprise traction mechanism plates 19, 19' which are arranged on and securely connected to the back sides of the bevel gear rims 15, 15'.

Figure 3:
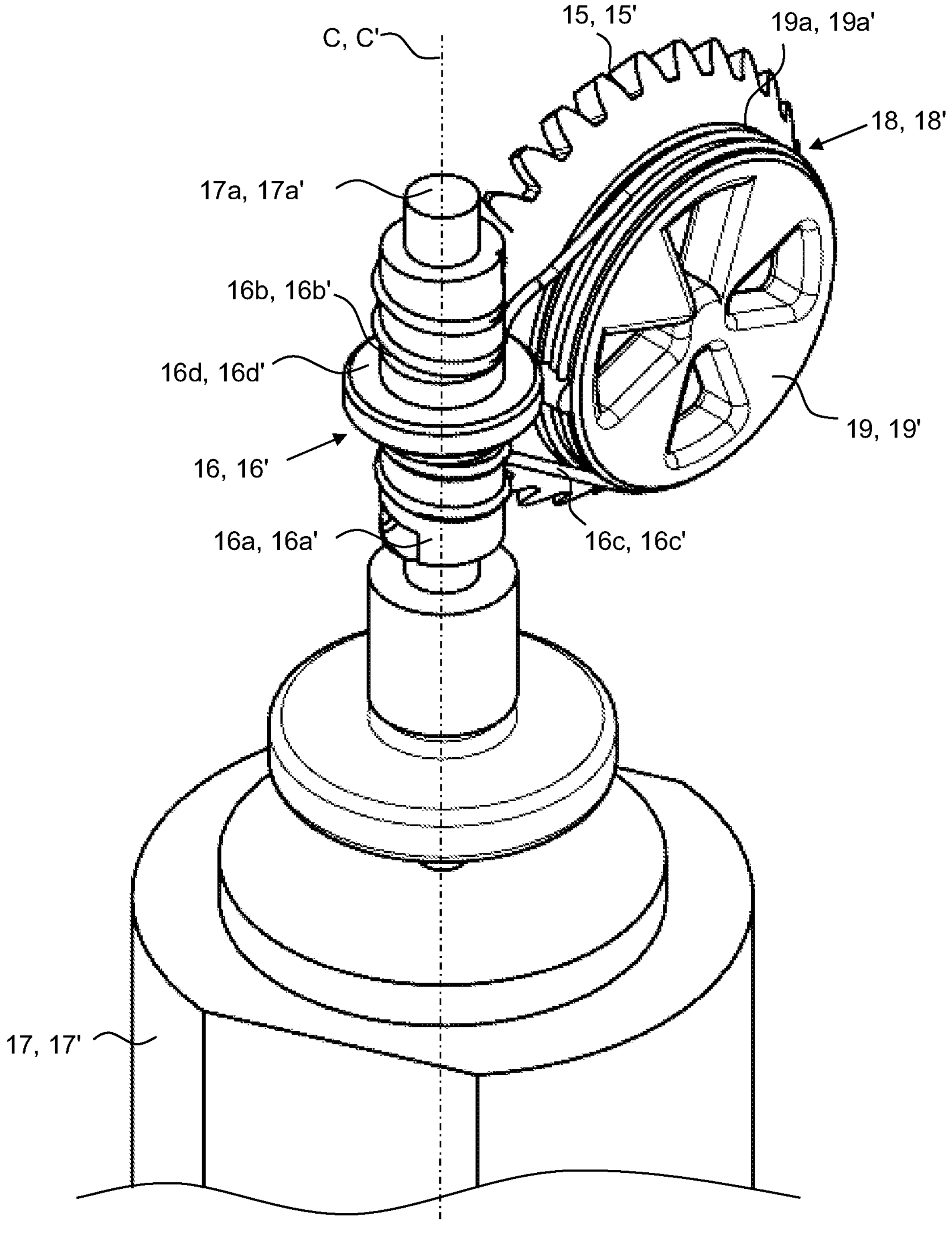
FIG. 3 shows a perspective detailed view of a traction mechanism drive.

As may be seen particularly well in the detailed illustration in FIG. 3, each traction mechanism plate 19, 19' has grooves **19*a*, 19*a*', in which traction mechanisms 16*c*, 16*c*', for example a cable or a belt, are guided. Each traction mechanism 16*c*, 16*c*' connects the respective traction mechanism plate 19, 19' to a spindle 16*a*, 16*a*', which is part of a traction mechanism drive 16, 16'. The spindles 16*a*, 16*a*' comprise grooves 16*b*, 16*b*' introduced into the body of the spindles 16*a*, 16*a*' in helical form. Additionally, a spindle nut 16*d*, 16*d*' arranged around a central portion of the spindle 16*a*, 16*a*' is provided to prevent the traction mechanisms 16*c*, 16*c*' from slipping from the spindle 16*a*, 16*a*'. In principle, the traction mechanism can be provided by a closed cable or a closed belt, which entwines the spindle and the drive rim. In the illustrated example, the traction mechanism 16*c*, 16*c*' is an open cable or belt with two ends, one traction mechanism end 16*e*' of which is visible in FIG. 4 at the upper end of the back spindle 16'. The cable or belt ends 16*e*' are each fastened by sliding blocks (not visible) in a groove portion of the spindle groove 16*b*, 16*b*' delimited by the spindle nut 16*d*, 16*d*', while the traction mechanism 16*c*, 16*c*' entwines the drive rim 19*a*, 19*a*'. Naturally, the spindle can alternatively be entwined by the traction mechanism while the traction mechanism ends are fastened by sliding blocks in the groove of the drive rim 19*a*, 19*a*'** formed as traction mechanism plate. Further, there is also the option of using two traction mechanisms, wherein one respective traction mechanism end is fastened in the spindle groove and the other in the traction mechanism plate groove by way of sliding blocks.

The spindles **16*a*, 16*a*' are driven by motors 17, 17', wherein the spindles 16*a*, 16*a*' are seated on drive shafts 17*a*, 17*a*', which are directly connected to the motors 17, 17' and make the spindles 16*a*, 16*a*' rotate or oscillate. Actuating a spindle 16*a*, 16*a*' causes the traction mechanism 16*c*, 16*c*' to be wound onto one end of the spindle 16*a*, 16*a*' and unwound from the other end, whereby the traction mechanism 16*c*, 16*c*' transfers the drive movement via the drive rim 19*a*, 19*a*' embodied as traction mechanism plate to the drive wheel 18, 18'. The axis of rotation C, C' of the drive bevel gears 16, 16' is the same as the axis of rotation of the motors 17, 17'. In FIGS. 2 and 4, these axes of rotation C, C' are perpendicular, which is to say at right angles, to the common axis A and perpendicular to the longitudinal axis B, and hence also parallel to an axis of rotation D of the third gear wheel 25 and fourth gear wheel 31 in the depicted neutral position of the wobble plate 14**.

Naturally, arrangements deviating from the depicted examples of the motors 17, 17' and spindles **16*a*, 16*a*' operatively connected to the traction mechanism plates 19, 19' are also conceivable. The arrangement of the drive units made of motor and spindle can be chosen freely along the circumference of the respective double gear wheel, with the result that an available installation space can be optimally used or the dimensions of the actuation unit can be reduced. That is to say, unlike in the case of a direct drive of the bevel gears 15, 15', the axes of rotation C, C' need not be parallel to the center axis A of the double gear wheels 18, 18' or to the longitudinal axis B of the instrument but can in theory be arranged in any desired orientation and also independently of one another on the double gear wheels 18, 18'. However, the arrangement example depicted in FIGS. 2 to 4 may be preferable for structural reasons since the arrangement of the motors 17, 17' next to one another parallel to the axis of rotation D, according to FIGS. 2 to 4, reduces the installation height, even though this is also achieved by an arrangement of the motors 17, 17' parallel to the longitudinal axis B. However, it is also conceivable that one of the drive units made of motor and spindle is offset through 180° in relation to the double gear wheels 18, 18' such that the motor-spindle-traction mechanism plate arrangements are diametrically offset and point in opposite directions, especially in an arrangement of the motors 17, 17'** parallel to the longitudinal axis B, since the installation height is not increased as a result.

The spindles 16*a*, 16*a'* are driven by motors 17, 17' by way of drive shafts 17*a*, 17*a'* of the motors 17, 17' whose respective axis of rotation corresponds to an axis of rotation C, C' of the motors 17, 17'. By rotating the spindle 16*a*, 16*a'*, in the helical groove 16*b*, 16*b'* of which the traction mechanisms 16*c*, 16*c'* are guided, the traction mechanism 16*c*, 16*c'* is unwound at one end of the spindle 16*a*, 16*a'* and wound up at the other end of the spindle 16*a*, 16*a'*, with the result that a directed tension arises at the traction mechanism plate 19, 19' via the traction mechanism 16*c*, 16*c'* and said traction mechanism plate can be made to rotate or oscillate. Thus, the rotation of the motors 17, 17' about their respective axis of rotation C, C, and hence the rotation of the spindles 16*a*, 16*a'*, is transferred to the double gear wheels 18, 18' about their respective axis of rotation A. The rotational movement of the double gear wheels 18, 18' then brings about a rotational movement of the third gear wheel 25 or fourth gear wheel 31 about its axis of rotation D, which is at right angles to the common axis A of the double gear wheels 18, 18', and hence brings about a movement of the wobble plate 14. In FIG. 2, these axes of rotation C, C' are parallel to an axis of rotation D of the third gear wheel 25 and fourth gear wheel 31. In FIG. 3, the drive axes C, C' are arranged parallel to the instrument axis B and hence at right angles to the axis of rotation D of the third gear wheel 25 and fourth gear wheel 31, and to the common axis of rotation A of the double gear wheels 18, 18'.

The structure and operation of the steering gear 13 in relation to the control of the wobble plate 14 that is actuatable by the drive units and in relation to the mounting of said wobble plate are described below on the basis of FIGS. 4 and 5, wherein the bevel gears with the bevel gear rims 15, 15' of the double gear wheels 18, 18' are depicted in FIG. 5.

A hollow main shaft 21 which extends coaxially with respect to the longitudinal axis B of the shaft 2, which is rotatable about the longitudinal axis B of the shaft 2, and which extends beyond the proximal end 3 of the shaft 2 into the region of the steering gear 13 is arranged in the shaft 2 of the instrument 1. The actuation element 8 for actuating the instrument 7 is axially displaceably mounted within this hollow main shaft 21.

The steering wires 12 that emerge from the shaft 2 at the proximal end 3 of the shaft 2, for the purposes of which a shaft end piece 3 in which passage slots 33 for the steering wires 12 are provided can be provided at the proximal shaft end, are fanned open in the depicted examples by way of a fan plate 22 arranged for conjoint rotation with the main shaft 21 on the shaft end piece 3, thereby increasing the radial distance of the steering wires 12 from the longitudinal axis B of the shaft 2. While the diameter of the bundle of steering wires 12, which coaxially surround the longitudinal axis B of the shaft 2, is for example 4 mm within the shaft 2 or at the distal end 5 in the region of the deflection mechanism 9, the diameter of the bundle formed by the steering wires 12 is for example 18 mm behind the fan plate 22. In the illustrated exemplary embodiment, the bundle consists of ten individual steering wires 12. The increase in the radial distance of the steering wires 12 from the longitudinal axis B of the shaft 2 obtained with the aid of the fan plate 22 not only simplifies the assembly and fabrication of the gear 13 equipped with the wobble plate 14 but also proportionally reduces the adjustment angle of the wobble plate 14 required for obtaining a desirably large pivot angle of the pool tip 6. With the increase in the diameter of the steering wire bundle from 4 mm within the shaft 2 to 18 mm behind the fan plate 22 described in exemplary fashion, the adjustment angle of the wobble plate 14 accordingly reduces 4.5-fold vis-à-vis the pivot angle of the tool tip 6 obtainable at the distal end. Thus, a pivot of the wobble plate 14 through only 20° is required to deflect said tool tip through 90°.

On the proximal side behind the fan plate 22, the steering wires 12 running parallel to the longitudinal axis B of the shaft 2 are supplied to the wobble plate 14. In an alternative not depicted here, the steering wires 12 emerging at the proximal end 3 can run directly to the wobble plate 14 without the fan plate, with the result that the steering wires are supplied to the wobble plate 14 at an angle with respect to the longitudinal axis B. To secure the steering wires 12 on the wobble plate 14, drilled through holes 23 are formed in the wobble plate 14 for each steering wire 12, with the steering wires 12 in the example shown being frictionally connected and affixed to the wobble plate 14 within the drilled through holes 23 by way of setscrews 24. For example, alternative forms of fastening the steering wires to the wobble plate also comprise welding or crimping or other clamping devices.

The double gear wheels 18, 18' as drive wheels are coupled to the third gear wheel 25 which by preference is in the form of a bevel gear and which meshes with the two bevel gear rims 15, 15' of the double gear wheels 18, 18', with the result that the axis of rotation D of the third gear wheel 25 intersects the common axis of rotation A of the double gear wheels 18 and 18' and the longitudinal axis B of the shaft 2. As a result of the three meshing gear wheels 18, 18', and 25, every movement of the two double gear wheels 18, 18' is directly transmitted to the wobble plate 14 that is coupled to the third gear wheel 25, bringing about a direct actuation of the steering wires 12.

To form a gimbal mount of the wobble plate 14 on the main shaft 21, the wobble plate 14 is pivotably mounted on a universal joint plate 28 by way of two bearing pins 27 arranged offset from one another by 180°, said universal joint plate in turn being pivotably mounted on the main shaft 21 by way of two bearing pins 29 arranged offset from one another by 180°. In FIG. 5, only one bearing pin 27 and one bearing pin 29 can be seen in each case on account of the partial sectional view.

In this case, the bearing pins 27 of the wobble plate 14 and the bearing pins 29 of the universal joint plate 28 are arranged offset from one another by 90°. This mount allows the wobble plate 14 to be pivoted relative to the longitudinal axis B of the shaft 2 about two axes at right angles to one another and allows a rotation of the main shaft 21 about the longitudinal axis B to be transmitted to the wobble plate 14, whereby, by way of the steering wires 12, the tool tip 6 (cf.

FIG. 1) is pivotable in all spatial directions relative to the longitudinal axis B of the shaft 2 on the distal side.

The steering gear 13 depicted in FIG. 4 has an alternative gimbal mount of the wobble plate 14 on the main shaft 21. This bearing arrangement, which is structurally simpler, more compactly designed, and easier to assemble, also allows pivoting of the wobble plate 14 about two degrees of freedom and rotation of said wobble plate about the longitudinal axis B, whereby, by way of the steering wires 12, the tool tip 6 is pivotable in all spatial directions relative to the longitudinal axis B of the shaft 2 on the distal side. In the region provided for mounting the wobble plate 14, the main shaft 21 in this case comprises two guide grooves 20*a* which extend along the main shaft 21 and introduced into the main shaft 21 on both sides or diametrically, two pins 29 arranged diametrically on the wobble plate 14 in radially inwardly pointed fashion engaging in said guide grooves, with only one guide groove 20*a* with the pin 29 engaging therein being visible in FIG. 4. As a result of this engagement, the wobble plate 14 can be pivoted about both the axis of rotation D and the axis of rotation A from a neutral position, in which the wobble plate 14 is located in a plane which is defined by the axis of rotation A and perpendicular, which is to say at right angles, to the longitudinal axis B. Overlaid movements as a result of pivoting about both axes of rotation A, D are likewise possible. Further, the engagement of the pins 29 in the guide grooves 20*a* enables the transfer of a rotary angle of the main shaft 21 to the wobble plate 14, with the result that the wobble plate 14 can be displaced three-dimensionally relative to the longitudinal axis B of the shaft 2. The maximum tilt or twist or the maximum tilt and rotary angles about the axes of rotation A and D are determined by the length and depth of the guide grooves 20*a* in conjunction with the internal diameter and thickness of the wobble plate 14 and length of the pins 29. In the depicted example, the main shaft 21 comprises a spherical portion 20*b* in the region provided for mounting the wobble plate 14, the guide grooves 20*a* being present in said spherical portion and the latter securing the wobble plate 14 in the axial direction. In this case, the wobble plate 14 has a contoured accommodation recess matched to the spherical portion 20*b*.

As is also evident from FIGS. 4 and 5, the spatially adjustable wobble plate 14 is mounted in a steering ring 30 that is coupled for conjoint rotation with the third gear wheel 25. To close the gear chain formed by the double gear wheels 18, 18' and gear wheel 25 to form a closed gear ring which ensures a uniformly all-round force distribution, the fourth gear wheel 31, which is likewise by preference designed as a bevel gear and meshes with the bevel gear rims 15, 15' of the two double gear wheels 18 and 18', is arranged on the axis of rotation D of the third gear wheel 25 opposite to the third gear wheel 25.

By way of a bearing ring 32, the wobble plate 14 is mounted in the steering ring 30 which is coupled for conjoint rotation with the third gear wheel 25, in order to allow a rotation of the wobble plate 14 about the longitudinal axis B of the shaft 2. The steering ring 30 coupled for conjoined rotation with the third gear wheel 25 is freely rotatable in relation to the fourth gear real 31 as a result of mounting by means of the bearing ring 42, with the result that a rotation of the fourth gear wheel 31 about its axis of rotation D does not bring about a twist of the steering ring 30 and wobble plate 14.

The described gimbal mount of the wobble plate 14 on the main shaft 21 allows the wobble plate 14 to be displaced three-dimensionally relative to the longitudinal axis B of the shaft 2. If, proceeding from the neutral initial position depicted in FIGS. 4 and 5, in which the wobble plate 14 is aligned perpendicular to the longitudinal axis B of the shaft 2, the double gear wheels 18, 18' are driven by way of the motors 17, 17' such that the double gear wheels 18, 18' rotate in the same direction, this twisting of the double gear wheels 18, 18', on account of the meshing engagement with the third gear wheel 25 and the fourth gear wheel 31, brings about a tilt of the assembly formed by the third gear wheel 25, the wobble plate 14 coupled to the third gear wheel 25 via the steering ring 30, and the fourth gear wheel 31, about the common axis of rotation A of the double gear wheels 18 and 18'. To simplify the functional description, the alignment of the bearing pins 27, 29 of the gimbal mount is referred to below in relation to the axes of rotation A and D. In fact, the bearing pins 27, 29 will no longer be flush with axes A and D as illustrated in the case of a rotation of the main shaft 21 and hence a rotation of the wobble plate 14, with the result that the pivot axes of the wobble plate 14 provided by the bearing pins 27, 29 may deviate from the axes of rotation A, D of the steering gear 13.

In the example of FIG. 5, this tilt of the wobble plate 14 relative to the main shaft 21 is enabled by the bearing pins 27, which are flush with the axis of rotation A of the double gear wheels 18, 18' and by means of which the wobble plate 14 is pivotably mounted on the universal joint plate 28. This tilt of the wobble plate 14 about the axis of rotation A relative to the longitudinal axis B of the shaft 2 brings about, distally and by way of the steering wires 12, a corresponding pivot of the tool tip 6 relative to the longitudinal axis B of the shaft 2. In the example of FIG. 4, the tilt of the wobble plate 14 about the axis of rotation A is enabled by the movement of the guide pins 29 in the guide grooves 20*a* in the spherical portion 20*b* of the main shaft 21.

If, proceeding from the neutral initial position depicted in FIGS. 4 and 5, in which the wobble plate 14 is aligned perpendicular to the longitudinal axis B of the shaft 2, the double gear wheels 18, 18' are driven by way of the motors 17, 17' such that the double gear wheels 18, 18' rotate in opposite directions, this twisting of both double gear wheels 18, 18', on account of the meshing engagement with the third gear wheel 25, brings about a twisting of the assembly formed by the third gear wheel 25 and the wobble plate 14 coupled to the third gear wheel 25 via the steering ring 30, about the axis of rotation D of the third gear wheel 25.

In the example of FIG. 5, this twist of the universal joint plate 28 relative to the main shaft 21 is enabled by the bearing pins 29, which are flush with the axis of rotation D of the third gear wheel 25 and by means of which the universal joint plate 28 is pivotably mounted on the main shaft 21, together with the free rotatability of the wobble plate 14 relative to the fourth gear wheel 31 on account of the bearing ring 32. This twist of the wobble plate 14 about the axis of rotation D relative to the longitudinal axis B of the shaft 2 brings about, distally and by way of the steering wires 12, a corresponding pivot of the tool tip 6 relative to the longitudinal axis B of the shaft 2. In the example of FIG. 4, the twist of the wobble plate 14 about the axis of rotation D is brought about analogously by the pins 29 which engage in the guide grooves 20*a* and which are flush with the axis of rotation D of the third gear wheel 25.

Naturally, it is possible to overlay the movements described, with the result that, by way of example, the wobble plate 14 is tilted about the common axis of rotation A of the double gear wheels 18, 18' and, at the same time, is also additionally twisted about the axis of rotation D of the third gear wheel 25. As a result of combining the two sequences of motion on account of the individually controllable motors 17, 17' of the gear 13 and the coupling with the main shaft 21, it is possible to three-dimensionally adjust the wobble plate 14 relative to the longitudinal axis B of the shaft 2, from which a corresponding spatial displacement of the tool tip 6 results on account of the coupling via the steering wires 12.

A surgical instrument 1 embodied as described above is distinguished in that many thin steering wires 12 can be used to control the pivotable tool tip 6 and that, on account of the motorized drive 13 for the wobble plate 14 on which the steering wires are mounted 12, this control can be sensitive, precise and reproducible.

An exemplary embodiment of the disclosure is depicted in the drawings. The drawings, the description, and the claims contain numerous features in combination. A person skilled in the art will advantageously also consider the features on an individual basis and combine them to form further advantageous combinations. The present disclosure provides a steering gear 13 for a surgical instrument 1 and the surgical instrument 1 itself. The steering gear 13 is arranged at the proximal end 3 of a shaft 2 which defines a longitudinal axis B and has a deflection mechanism 9 at the distal end 5. In this case, it has two motorized drives and is designed to spatially align a wobble plate 14, which controls the distal deflection mechanism 9 of the surgical instrument 1, via the adjustment angles of said drives. The first drive has a first drive shaft **17*a* which is driven by a first motor 17 and operatively connected to a first traction mechanism plate 19 of a first drive wheel 18 via a first traction mechanism 16*c* arranged between the first traction mechanism plate 19 and a first spindle 16*a* which is seated on the first drive shaft 17*a*, which defines a first drive axis C. The second drive has a second drive shaft 17*a'* which is driven by a second motor 17' and operatively connected to a second traction mechanism plate 19' of a second drive wheel 18' via a second traction mechanism 16*c'* arranged between the second traction mechanism plate 19' and a second spindle 16*a'* which is seated on the second drive shaft 17*a'*, which defines a second drive axis C'. In this case, the first and the second drive wheel 18, 18' are designed as double gear wheels 18, 18' and each comprise the corresponding traction mechanism plate 19, 19' and a bevel gear rim 15, 15' present on the respective backward side, wherein the wobble plate 14 is arranged between the two drive wheels 18, 18', which have a common axis of rotation A, and the bevel gear rims 15, 15'** are arranged facing one another on the axis of rotation A.

The invention claimed is:

1. A steering gear for a surgical instrument, arranged at a proximal end of a shaft which defines a longitudinal axis and has a deflection mechanism at a distal end of the shaft, wherein the steering gear comprises:

two motorized drives configured to spatially orient a wobble plate by way of a respective adjustment angle of the two motorized drives, the wobble plate is configured to control the distal deflection mechanism at the distal end of the shaft; wherein the two motorized drives include a first drive and a second drive, the first drive includes a first drive shaft which is driven by a first motor and operatively connected to a first traction mechanism plate of a first drive wheel via a first traction mechanism arranged between the first traction mechanism plate and a first spindle which is seated on the first drive shaft, which defines a first drive axis, and the second drive includes a second drive shaft which is driven by a second motor and operatively connected to a second traction mechanism plate of a second drive wheel via a second traction mechanism arranged between the second traction mechanism plate and a second spindle which is seated on the second drive shaft, which defines a second drive axis, wherein the first and the second drive wheel are designed as double gear wheels and each comprises the corresponding traction mechanism plate and a bevel gear rim present on a respective backward side, and wherein the wobble plate is arranged between the first drive wheel and the second drive wheel, which have a common axis of rotation, and the bevel gear rims are arranged facing one another on the axis of rotation.

2. The steering gear as set forth in claim 1, wherein the first traction mechanism and the second traction mechanism are closed or not closed belts or cables.

3. The steering gear as set forth in claim 1, characterized in that a drive axis of the first motor is present in parallel with a drive axis of the second motor.

4. The steering gear as set forth in claim 1, wherein each of the first spindle and the second spindle has a groove all round, in which the respective first traction mechanism and second traction mechanism is guided.

5. The steering gear as set forth in claim 1, wherein the spindle comprises a spindle nut.

6. The steering gear as set forth in claim 1, wherein each of the first traction mechanism plate and the second traction mechanism plate has a groove extending continuously along a circumference of the first traction mechanism plate and second traction mechanism plate, with which the first traction mechanism and the second traction mechanism is respectively in contact with.

7. The steering gear as set forth in claim 6, further including at least one sliding block, wherein at least one of the first traction mechanism and the second traction mechanism is open-ended, and the groove of a corresponding one of the first traction mechanism plate or the second traction mechanism plate receives the sliding block, the sliding block fastening an end of the non-closed traction mechanism to that traction mechanism plate.

8. The steering gear as set forth in claim 1, wherein each of the motors, by way of its respective spindle, is arrangeable in any radial position pointing away from the first traction mechanism plate and the second traction mechanism plate, wherein the first drive axis and the second drive axis run parallel to one another in a preferred arrangement.

9. The steering gear as set forth in claim 1, wherein the wobble plate is coupled to a third gear wheel which meshes with the two bevel gear rims of the double gear wheels and whose axis of rotation is at right angles to the common axis of the double gear wheels.

10. The steering gear as set forth in claim 9, wherein the wobble plate is coupled to a fourth gear wheel which is coupled to the two bevel gear rims of the two double gear wheels and arranged on the side facing away from the third gear wheel.

11. A surgical instrument comprising the steering gear of claim 1:

an actuation unit arranged at a proximal end of the shaft; and a tool arranged at the distal end of the shaft, the tool including a tool tip which is able to be deflected by means of the distal deflection mechanism and controllable by the wobble plate that is spatially alignable by means of the two motorized drives, the steering gear configured to transfer the adjustment angles of the two motorized drives to the spatial alignment of the wobble plate.

12. The surgical instrument as set forth in claim 11, further including a third gear wheel that meshes with the two bevel gear rims of the two double gear wheels, the wobble plate, via a bearing ring, is mounted so as to be rotatable about the longitudinal axis of the shaft in a steering ring that is coupled for conjoint rotation with the third gear wheel, the wobble plate being gimbal-coupled to a main shaft running coaxially with a longitudinal axis of the shaft.

13. The surgical instrument as set forth in claim 12, further including a fourth gear wheel that is coupled to the wobble plate via a bearing ring with the steering ring, wherein the fourth gear wheel is freely rotatable vis-à-vis the third gear wheel.

14. The surgical instrument as set forth in claim 11 wherein the wobble plate is pivotably mounted on a universal joint plate by way of two bearing pins arranged offset from one another by 180°, wherein the universal joint plate is pivotably mounted on the main shaft by way of two bearing pins arranged offset from one another by 180°, and wherein the bearing pins of the wobble plate and universal joint plate are arranged offset from one another by 90°.

15. The surgical instrument as set forth in claim 11, further including an actuation element that is axially displaceably mounted in the shaft and is operatively connected to the actuation unit on the proximal end, and wherein a distal deflection mechanism of the tool tip includes pivot members arranged at the distal end of the shaft and connected to the wobble plate of the steering gear by steering wires running along the longitudinal direction of the shaft.

16. The surgical instrument as set forth in claim 15, wherein a radial distance of the steering wires from the longitudinal axis of the shaft at the wobble plate is greater than at the proximal end of the shaft, from which the steering wires emerge, wherein the steering wires extend directly from the proximal end of the shaft to the wobble plate and form an angle of less than 90° relative to a plate surface of the wobble plate.

17. The surgical instrument as set forth in claim 15, wherein a fan plate is arranged on a main shaft distally in front of the wobble plate, the fan plate increasing the radial distance of the steering wires from the longitudinal axis such that the steering wires run approximately parallel between the fan plate and the wobble plate and form an angle of about 90° relative to a plate surface of the wobble plate.

18. The surgical instrument as set forth in claim 11, further including a gimbal mount, the gimbal mount is provided by two longitudinally extending guide grooves diametrically present in the main shaft and two diametrically and radially inwardly pointing pins arranged on the wobble plate, wherein each pin engages in one of the guide grooves such that a rotational angle of the main shaft is transferable to the wobble plate.

* * * * *